(12) United States Patent
Rajasekharan et al.

(10) Patent No.: US 12,399,110 B2
(45) Date of Patent: Aug. 26, 2025

(54) ELECTROCHEMICAL DIGESTION

(71) Applicant: Hach Company, Loveland, CO (US)

(72) Inventors: Vishnu Vardhanan Rajasekharan, Fort Collins, CO (US); Dan Jonathan Kroll, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 0 days.

(21) Appl. No.: 17/551,973

(22) Filed: Dec. 15, 2021

(65) Prior Publication Data

US 2022/0187197 A1 Jun. 16, 2022

Related U.S. Application Data

(60) Provisional application No. 63/126,317, filed on Dec. 16, 2020.

(51) Int. Cl.
| | |
|---|---|
| *G01N 21/31* | (2006.01) |
| *G01N 27/30* | (2006.01) |
| *G01N 27/49* | (2006.01) |

(52) U.S. Cl.
CPC ........... *G01N 21/31* (2013.01); *G01N 27/308* (2013.01); *G01N 27/49* (2013.01)

(58) Field of Classification Search
CPC ...... G01N 21/31; G01N 27/308; G01N 27/49; G01N 1/4044; G01N 27/42; G01N 21/78;
(Continued)

(56) References Cited

U.S. PATENT DOCUMENTS

| | | | |
|---|---|---|---|
| 2008/0237060 A1* | 10/2008 | Hegel | C02F 1/645 |
| | | | 205/744 |
| 2015/0111304 A1* | 4/2015 | Leggett | G01N 33/1846 |
| | | | 436/146 |

(Continued)

FOREIGN PATENT DOCUMENTS

| | | | |
|---|---|---|---|
| CN | 104478178 A | * | 4/2015 |
| CN | 209974381 U | * | 1/2020 |

(Continued)

OTHER PUBLICATIONS

Schaefer et al., Electrochemical treatment of perfluorooctanoic acid and perfluorooctane sulfonate: insights into mechanisms and application to groundwater treatment, Chemical Engineering Journal, 2017, 317, 424-432 (Year: 2017).*

(Continued)

*Primary Examiner* — Luan V Van
*Assistant Examiner* — Shizhi Qian
(74) *Attorney, Agent, or Firm* — Ference & Associates LLC

(57) ABSTRACT

An embodiment provides a method for digesting at least one analyte of an aqueous sample, including: introducing an aqueous sample comprising at least one analyte into a digestion device comprising one or more carbon substituted material electrodes; digesting the at least one analyte by applying an electrical potential between an anode and a cathode of the digestion device, wherein the digesting comprises a step-wise disintegration; measuring the at least one analyte of the aqueous sample from the digested material, using a measurement device selected from the group consisting of: an electrochemical device and an optical measurement device; and modifying the electrical potential based upon the measurement of the at least one analyte. Other aspects are described and claimed.

18 Claims, 5 Drawing Sheets

(58) Field of Classification Search
CPC ........... G01N 33/1806; G01N 33/1813; G01N 33/1846; G01N 27/44

See application file for complete search history.

(56) References Cited

U.S. PATENT DOCUMENTS

| | | | |
|---|---|---|---|
| 2015/0136591 A1* | 5/2015 | Fraim | C25B 9/17 204/290.01 |
| 2019/0033249 A1* | 1/2019 | O'Mahony | G01N 27/416 |
| 2019/0136393 A1* | 5/2019 | Dopp | C25B 3/23 |
| 2019/0330086 A1* | 10/2019 | Stephenson | C02F 9/00 |
| 2019/0389751 A1* | 12/2019 | Kiely | G01N 33/1806 |
| 2020/0173891 A1* | 6/2020 | Schuelke | G01N 1/40 |
| 2020/0283314 A1* | 9/2020 | Kiely | C02F 3/305 |

FOREIGN PATENT DOCUMENTS

| | | | | |
|---|---|---|---|---|
| KR | 20130025019 A | * | 3/2013 | |
| KR | 102143036 B1 | * | 8/2020 | |
| WO | WO-2010080327 A1 | * | 7/2010 | .......... G01N 27/305 |
| WO | WO-2016005662 A1 | * | 1/2016 | .............. B03D 1/14 |
| WO | WO-2019178280 A1 | * | 9/2019 | .............. C07K 1/12 |
| WO | WO2020023601 A1 | | 1/2020 | |

OTHER PUBLICATIONS

Grube et al., The challenge of achieving safely managed drinking water supply on San Cristobal island, Galápagos, International Journal of Hygiene and Environmental Health, 2020, 228, 113547 (Year: 2020).*

Yan et al., Colorimetric Method for Determining Pb2+ Ions in Water Enhanced with Non-Precious-Metal Nanoparticles, Analytical Chemistry, 2012, 84, 6122-6127. (Year: 2012).*

Park et al., English translation of KR102143036B1, 2020 (Year: 2020).*

Cai et al., English translation of CN104478178A, 2015 (Year: 2015).*

European Patent Office, International Search Report and Written Opinion, Apr. 22, 2022, 14 pages.

Charles E. Schaefer et al., "Electrochemical treatment of perfluorooctanoic acide and perfluorooctane sulfonate: Insights into mechanisms and application to groundwater treatment", Chemical Engineering Journal, 2017, 10 pages, Elsevier B.V.

* cited by examiner

ELECTROCHEMICAL DIGESTION

CROSS REFERENCE TO RELATED APPLICATION

This application claims priority to U.S. Provisional Patent Application Ser. No. 63/126,317, filed on Dec. 16, 2020, and entitled "ELECTROCHEMICAL DIGESTION," the contents of which are incorporated by reference herein.

FIELD

This application relates generally to water quality measurement, and, more particularly, to measurement of an analyte in an aqueous sample using electrochemical digestion.

BACKGROUND

Ensuring water quality is critical in a number of industries such as pharmaceuticals and other manufacturing fields. Additionally, ensuring water quality is critical to the health and well-being of humans, animals, and plants which are reliant on the water for survival. Inorganic and organic species of a sample may exist in non-measurable forms. For example, many of perfluorinated compounds may exist in oligomeric or polymeric forms. Measuring these complex forms is challenging and needs to be broken down to simpler forms that can be analyzed easily. Many of the inorganic species either exist as particulates or bound to other molecules through ligation. Analysis of this type of contaminants may be challenging because to the complexity of the analysis. These species are important to identify as they pose a serious threat to human health when they consume water contaminated with these species. Additionally, interferants in a water sample may interfere with proper measurement techniques.

BRIEF SUMMARY

In summary, one embodiment provides a method for digesting at least one analyte of an aqueous sample, comprising: introducing an aqueous sample comprising at least one analyte into a digestion device comprising one or more carbon substituted material electrodes; digesting the at least one analyte by applying an electrical potential between an anode and a cathode of the digestion device, wherein the digesting comprises a step-wise disintegration; measuring the at least one analyte of the aqueous sample from the digested material, using a measurement device selected from the group consisting of: an electrochemical device and an optical measurement device; and modifying the electrical potential based upon the measurement of the at least one analyte.

Another embodiment provides a measurement device for digesting at least one analyte of an aqueous sample, comprising: a digestion device; one or more carbon substituted material electrodes; a processor; and a memory device that stores instructions executable by the processor to: introduce an aqueous sample comprising at least one analyte into a digestion device comprising one or more carbon substituted material electrodes; digest the at least one analyte by applying an electrical potential between an anode and a cathode of the digestion device, wherein the digesting comprises a step-wise disintegration; measure the at least one analyte of the aqueous sample from the digested material, using a measurement device selected from the group consisting of: an electrochemical device and an optical measurement device; and modifying the electrical potential based upon the measurement of the at least one analyte.

A further embodiment provides a product for digesting at least one analyte of an aqueous sample, comprising: a digestion device; an anode; a cathode; and a storage device having code stored therewith, the code being executable by the processor and comprising: code that introduces an aqueous sample comprising at least one analyte into a digestion device comprising one or more carbon substituted material electrodes; code that digests the at least one analyte by applying an electrical potential between the anode and the cathode of the digestion device, wherein the digesting comprises a step-wise disintegration; code that measures the at least one analyte of the aqueous sample from the digested material, using a measurement device selected from the group consisting of: an electrochemical device and an optical measurement device; and code that modifies the electrical potential based upon the measurement of the at least one analyte.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
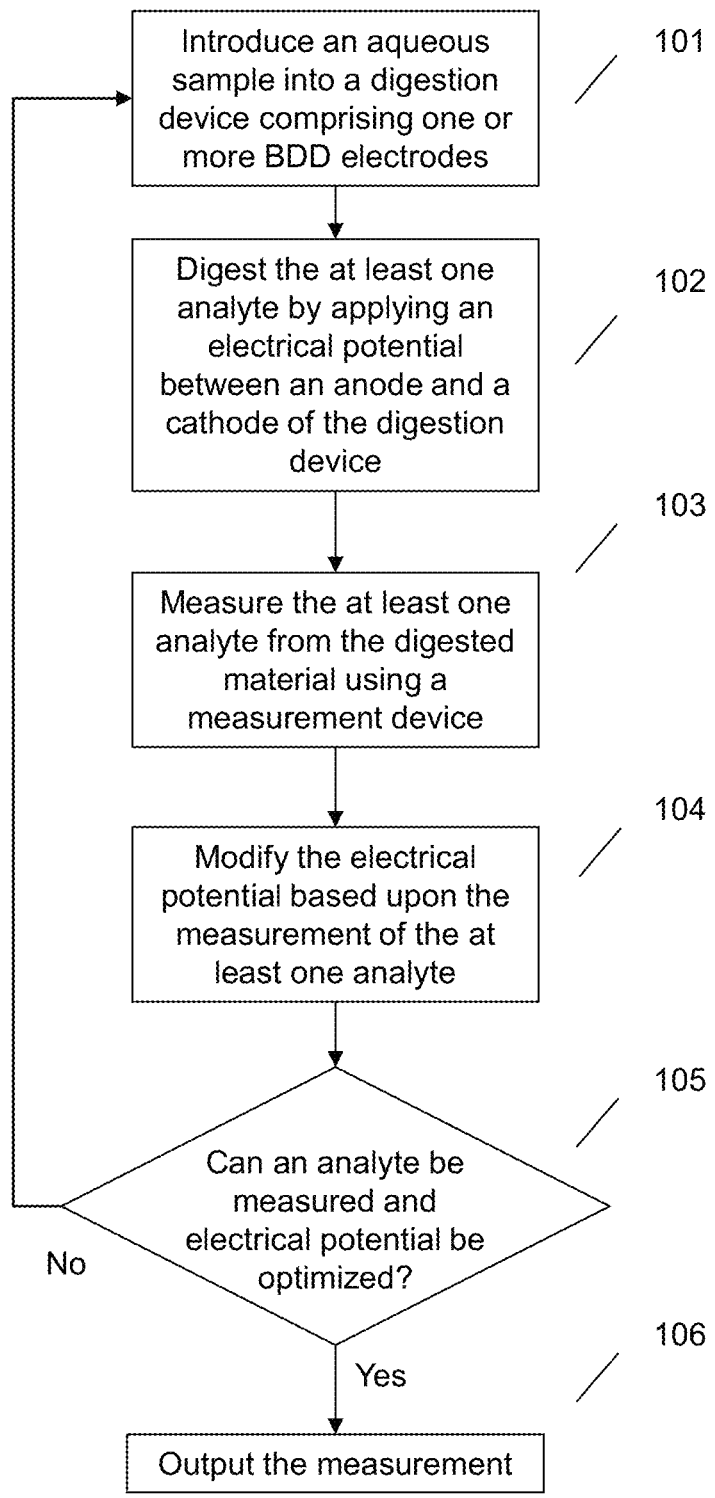
FIG. 1 illustrates a flow diagram of an example measurement of an analyte.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Ensuring water purity is critical in many applications, for example in municipalities that provide drinking water and in numerous other industries such as pharmaceuticals, chemicals and other manufacturing fields. The presence of organic compounds in the water may suggest a failure in filtration and/or other components and systems that, if left unchecked, can damage expensive industrial systems, impact product quality, be detrimental to public health, and even affect profit margins. As an example, drinking water quality will deteriorate if organics are present, such as perfluorinated compounds or other bound/particulate materials. Therefore, detecting the presence and concentration of these complex contaminants in water samples is vital. Total organic carbon (TOC) analysis is the measurement of the level of organic molecules or contaminants in purified water and is often used as a non-specific indicator of water quality. Chemical oxygen demand (COD) tests may be a measure of the oxygen equivalent of the organic matter content of a sample susceptible to oxidation by the strong chemical oxidant. Thus, COD tests may use a strong chemical oxidant in an acid solution with heat to oxidize organic material to carbon dioxide, water, and other oxidation products. In an embodiment, complex species may be broken down to a simpler form to enable the analysis. In an embodiment, the break down to simpler forms may be referred to as digestion. In an embodiment, oxidation may be a form of digestion. IN an embodiment, digestion may be referred to as disintegration. In an embodiment, the digestion may be step-wise. In other words, one or more analytes within an aqueous sample may be digestion in a sequential manner.

Solid state reagent-less digestion techniques may utilize a thin diamond-film electrode doped with boron to carry out the oxidation of the organic material to produce carbon dioxide (e.g., by generating hydroxyl radicals and ozone on the surface of the boron doped diamond (BDD) electrode). The system can then measure the amount of analyte present and correlate this measurement with a value or amount of complex species that are present in the aqueous sample. Previously available measurement devices may use boron doped diamond since it serves as a better electrode material than carbon-based or other metallic materials (e.g., silver, gold, mercury, nickel, etc.) because these materials poorly oxidize and may eventually themselves become oxidized.

The electrochemical measurement systems may use electrodes such as boron doped diamond (BDD) electrodes to measure analytical parameters. Additionally or alternatively, the BDD electrodes may provide a means to perturb a system by providing electrical energy for oxidation of components of an aqueous sample. Systems focus on the use of a single source perturbation and detection. In other words, systems may use a separate component or system to perform the perturbation and detection functions. This single source approach limits the ability of a system to validate and gain confidence in a measurement.

Conventional methods to measure an analyte and/or interferant of an aqueous sample may require high energy or corrosive chemicals to convert a complex form of the analyte into a simpler form to be analyzed. For example, the high energy or corrosive chemicals may be needed to break down soluble, colloidal, particulate, organically bound, polymeric, oligomeric, an oxidation state, or the like of an analyte. Extreme temperatures may include temperature near 500 degrees Celsius, and hazardous chemicals may include concentrated acids or powerful oxidants. Additionally, homogenization may use ultrasonic or high energy mixing techniques to represent a homogenous sample. These conditions pose a safety concern for a facility both in the implementation and storage of such materials. Maintaining safety represents both a cost to a facility and labor intensive conditions. A facility may have to store and prepare large quantities of highly hazardous reagents such as sulfuric acid, nitric acid, phosphoric acid, hydrogen peroxide, per sulfate, or the like. The hazardous materials may also be at a highly elevated temperature. Mixing of the reagents could result in explosive conditions. Some methods may require the use of an expensive catalyst such as platinum or the like. The conventional methods described are still subject to interferants that compromise analyte measurement accuracy. Many of these methods target measurement of metal ions and may not analyze oligomeric persistent, bio-accumulative, toxic, refractory organic material such as per fluorinated compounds like PFOS (Perfluorooctanesulfonic acid). What is needed is a method to accurately measure an analyte which may contain both interferants and soluble, colloidal, particulate, organically bound, polymeric, oligomeric, and various oxidation states found in the analyte, and may leverage heating and cavitation processes to convert the analyte desired to be measured into a simpler form.

Accordingly, the systems and methods described herein provide a technique for digesting and measuring an analyte of an aqueous sample. In an embodiment, the system and method may eliminate interferences. An aqueous sample may be introduced to a digestion chamber. At least one component of the aqueous sample may be oxidized. Oxidation of an analyte or multiple analytes of the aqueous sample may be performed simultaneously or sequentially. The system and method may measure an analyte. The measurement may use an electrochemically device, optical measurement device or the like. Bubbles and/or cavitation may facilitate an analyte digestion or oxidation. The system and method may modify or optimize the oxidation or digestion of an analyte based upon a measurement or digestion of an analyte. In an embodiment, the modifying may use an electrical potential to digest an analyte. In an embodiment the oxidation may be performed by applying an electrical signal between an anode and a cathode in contact with the aqueous sample. In an embodiment, the electrode may be a carbon substituted material or a BDD material.

In an embodiment, the aqueous sample may contain a complex form of the analyte. In an embodiment, an interferant may be electrochemically oxidized at various voltages in a step wise manner to convert the analyte into simpler forms as well as the proper oxidation state for analysis. Step wise oxidation may also allow the conversion of the interferant into species that may be either measure or eliminated. The analyses may be carried out in a stopped flow design. The system may contain electrodes that are capable of handling voltages that may sequentially or simultaneously oxidize the complex analyte and/or the interferant. Complex analytes may be converted to forms that can be analyzed by standard techniques. Interferants may be oxidized to a form that does not interfere during the analyte measurement.

The illustrated example embodiments will be best understood by reference to the figures. The following description is intended only by way of example, and simply illustrates certain example embodiments.

Referring now to FIG. 1, in an embodiment a system and method for oxidizing or digesting and measuring at least one analyte of an aqueous sample. At 101, an aqueous sample may be introduced into a chamber of a digestion or oxidation device. See FIG. 2 and FIG. 3. The aqueous sample may be placed or introduced into a test chamber manually by a user or using a mechanical means, for example, gravity flow, a pump, pressure, fluid flow, or the like. In an embodiment, the oxidation chamber or device may have a sample inlet for conveying an aqueous sample to the chamber. In an embodiment, the chamber may have a sample outlet. In an embodiment, the sample outlet may convey a digested sample to a measurement device or chamber. The measurement may be performed using electrochemical, colorimetric, or the like techniques. In an embodiment, the chamber may have a reagent inlet. In an embodiment, inlets and outlets may have associated valves, piping, controls, or the like.

In an embodiment, the digestion or oxidation chamber may be a column shape. A column shape is an example and other shapes are contemplated and disclosed. In an embodiment, the column may form a chamber and constructed of glass, acrylic, or the like. In an embodiment, the aqueous sample may be introduced into a space between two BDD electrodes. In an embodiment, a BDD electrode may be a type of substituted carbon material electrode. In an embodiment, the BDD electrodes may be encompassed in an inert material. The inert material may be selected such that it does not degrade during the method. In the column example, the BDD electrode may be a disc shape. The discs may be 1-2 cm in diameter. In an embodiment, there may be two BDD electrodes representing an anode and a cathode. In an embodiment, a power supply may provide an electrical signal or protocol to the anode and cathode. Each BDD electrode may be affixed to a block. The block may allow the movement of the BDD electrode. For example, the space between the BDD electrode and thus the space in which the aqueous sample may be present may be changed. In other words, the electrode position and distance from another electrode may be changed.

The aqueous sample may be an aqueous sample which may include a sample from a natural body of water, a holding tank, a processing tank, a pipe, or the like. The aqueous sample may be in a continuous flow, a standing volume of liquid, or any combination thereof. In one embodiment, the solution may be introduced to one or more chambers, vessels, or piping for example, a measurement chamber of the oxidation device. Introduction of the aqueous sample into the oxidation device may include placing or introducing the solution into the oxidation device manually by a user or using a mechanical means, for example, gravity flow, a pump, pressure, fluid flow, or the like. For example, a water sample for oxidation may be introduced to an oxidation, measurement, or test chamber using a pump. In an embodiment, valves or the like may control the influx and efflux of the solution into or out of the one or more chambers, vessels, or piping, if present. In an embodiment, there may be a gas outlet.

At 102, the method and system may digest at least one analyte. In an embodiment, the sample may have one or more analytes to be digested. The one or more analytes may be digested in a step-wise manner, such as sequentially. For example, the system and method may digest an analyte, and then proceed to digest another analyte. The digestions for a given analyte may repeat until analytes of interested are digested and/or measured. The system and method may use oxidation as a digestion technique. The oxidation may be performed by applying an electrical potential to the aqueous sample in a digestion chamber. In an embodiment, digestion may be performed by additional methods such as cavitation, heat, or the like. The electrical potential may be applied to one or more electrodes of the measurement device. The one or more electrode may be a BDD electrode. In an embodiment, the electrodes may be fully or at least partially disposed in the volume of aqueous sample. For example, if the aqueous sample is introduced into a chamber having one or more electrodes, the aqueous solution may at least partially cover the one or more electrodes. As another example, the one or more electrodes may be partially disposed within the chamber with the other portion of the electrode outside the chamber. Thus, when the aqueous sample is introduced into the chamber it only covers the portion of the electrodes that are within the chamber.

In an embodiment, oxidant species, such as hydroxyl radicals, may be generated by oxidation of water of the aqueous sample with an analyte. Additionally, with the production of oxidants the analyte may be directly oxidized and converted to simpler forms. In an embodiment, an interferant, such as chloride, also may be directly oxidized and converted to inert or measured at a different analytical space that is spatiotemporally separated from an analyte measurement. In an embodiment, the production of hydroxyl radicals, oxygen may also be produced due to the oxidation of water. When the concentration of the oxygen in the solution exceeds a threshold solubility, oxygen bubbles may be generated. In an embodiment, these bubbles facilitate the homogenization of particulate materials. In an embodiment, during the oxidation of water, protons may be produced which then reduces the pH. This process facilitates the solubilization of the particulates to be analyzed.

As an example, particulate iron and lead that are filtered through 0.45 μM or 0.22 μm may be oxidized and converted to soluble forms of metal ion species using an acid, bubble, and oxidant generation using this method. The soluble species may then be analyzed or measured using standard colorimetric methods that provide the total concentration of all the lead species which may include micro and nano particulate, colloidal and soluble species.

As another example, oligomeric perfluoro compounds, such as perfluoro octanoic acid, perfluoro octane sulfonic acid may be oxidized to fluoride ions that can be measured using standard colorimetric method. In an embodiment, ultra-low detection of PFOS compounds may be required. Nano textured diamond substrates may be used to preconcentrate the PFOS for a duration to increase the signal sensitivity. To improve the signal to noise ratio, fluoride measurement before and after the oxidation/conversion of PFOS may be required. Since the signal would be low when compared to the background, removal of the existing fluoride ions in the sample may be required before the oxidation/conversion of the PFOS compounds. Additionally, passing the sample through a calcium based material will remove the existing fluoride in the sample through filtration/precipitation. This will increase the signal to background ratio for the ultra-low application. A metal oxide framework may be used to preconcentrate and amplify the PFOS signal. Impedimetric analysis on the BDD coated with MOF may ensure the preconcentration step which than may be oxidized preferentially to soluble fluoride species.

As a further example, during Total Organic Carbon (TOC) analysis chloride may be an interferant. Chloride can be preferentially oxidized to chlorine that then can be measured using standard colorimetric techniques. This quantification may then be used to account for the interferant for the total organic carbon oxidation and analysis.

Figure 2:
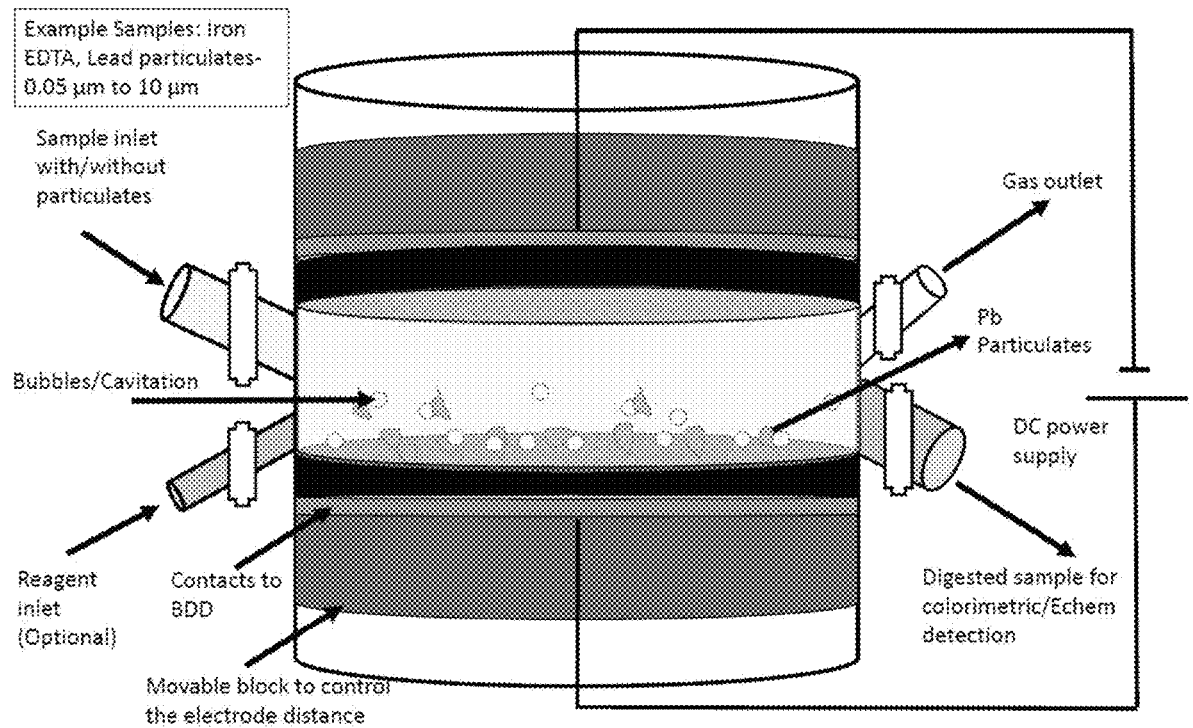
FIG. 2 illustrates an example device for a digestion cell.
Figure 3:
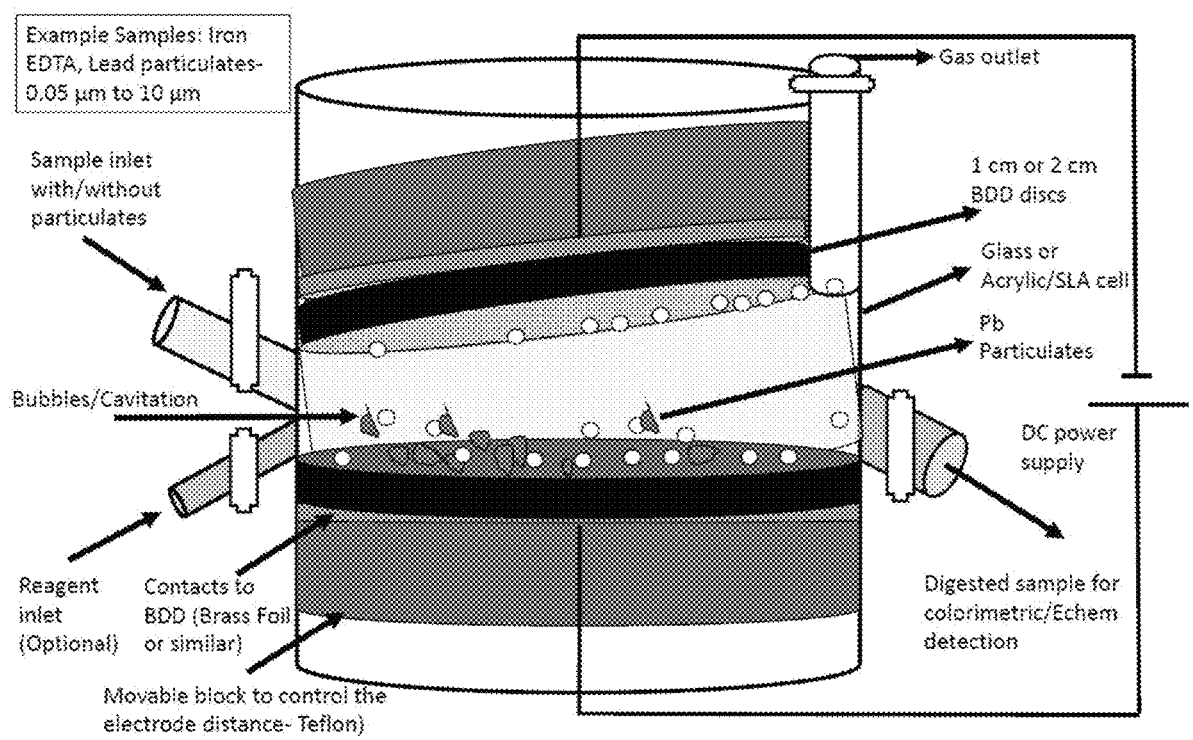
FIG. 3 illustrates another example device for a digestion cell.

In an embodiment, the electrical potential may be controlled using circuitry illustrated in FIG. 2 and FIG. 3. In an embodiment, the electrical signal may be a steady signal, a ramp, a pulse, or the like. The electrical potential may be applied until a threshold is reached. The threshold may be predetermined or a parameter/output may be recorded in real-time and adjust the electrical potential. An electrical potential may be altered based on reaction parameters such as components of the aqueous sample, condition of one or more electrodes, or the like.

In an embodiment, the electrodes may include an anode and a cathode of the digestion device. Thus, the electrical potential may pass between the anode and cathode through the aqueous sample. Referring to FIG. 2 and FIG. 3, the aqueous sample may be introduced into a chamber or compartment between two electrodes. The digestion device may have an anode and a cathode. The electrical potential between a cathode and an anode may electrochemically oxidize a metal, for example, the electrical signal may cause a transition metal to oxidize to a higher valent metal, for example, due to an electrochemical reaction. As an example, the transition metal may include iron, manganese, nickel, chromium, or the like.

An oxidation state or oxidation number may indicate a degree of oxidation. Oxidation is the loss of electrons in a chemical compound. An oxidation state, which may be a positive, negative, or zero value, may represent a charge an atom would have if all bonds were ionic with no covalent component. The transition metal may be on a boron doped diamond (BDD) substrate. Thus, using the example of the transition metal iron, the transition metal and BDD electrode in combination with an electrical potential may produce a thick plume of ferrate or manganate. A plume of ferrate may be produced at the anode. BDD is an intrinsically conductive or a semi-conductive substrate.

The higher valent metal may have a measurable color. In other words, while the transition metal itself may not have a color or be of a color that is not measurable, the higher valent metal may have a measurement color. Thus, the volume or amount of these higher valent metals may be measured, for example, using an infrared measurement device, spectrometer, colorimetric measurement device, or other optical measurement device. In other words, the higher valent metal species may be determined colorimetrically using visible spectroscopy to determine the concentration of the higher valent metals. In an embodiment, a digested sample outlet may convey a digested or oxidized analyte to a measurement device. In other words, measurement may not occur in the same chamber as the oxidation/digestion.

At 103, the system may determine whether an analyte of an aqueous sample can be measured. Example characteristics of an analyte that can be measured include pH, absorbance wavelength (color), total organic carbon (TOC), and the like. To measure the characteristic the system may employ a measurement device, for example, an electrochemical measurement device, an optical measurement device, or the like. In an embodiment, the characteristic may include the amount of organics in the aqueous sample. Since the organics are oxidized using the higher valent metal, the carbon dioxide may be measured electrochemically by meter electronics to determine TOC or COD. In an embodiment, the carbon dioxide may be measured optically to determine TOC or COD. For example, since the higher valent metal is of a measurable color, as the metal is used as a catalyst to oxidize the material in the aqueous sample, the higher valent metal is used, thereby causing a colorimetric change. This colorimetric change can be measured using different measurement devices. For example, the optical measurement may be performed using infrared measurement. In an embodiment, the Fe(VI), Mn(VII), and other transition metals may be visibly colored. For example, species in an aqueous sample may be determined colorimetrically using visible spectroscopy to determine the concentration of higher valent materials. For example, $Mn^{2+}$ may be a pale pink, $Mn(OH)_3$ containing Mn(III) as dark brown, $MnO_2$ containing Mn(IV) as black, Mn(VI) containing $(MnO_4)_2^-$ as green, Mn(VII) containing $MnO_4^-$ as purple, or the like. The resulting color from a reaction may be determined photometrically, for example, using a spectrophotometer. Alternatively or additionally, the resulting color from a reaction may be observed visually.

Figure 4:
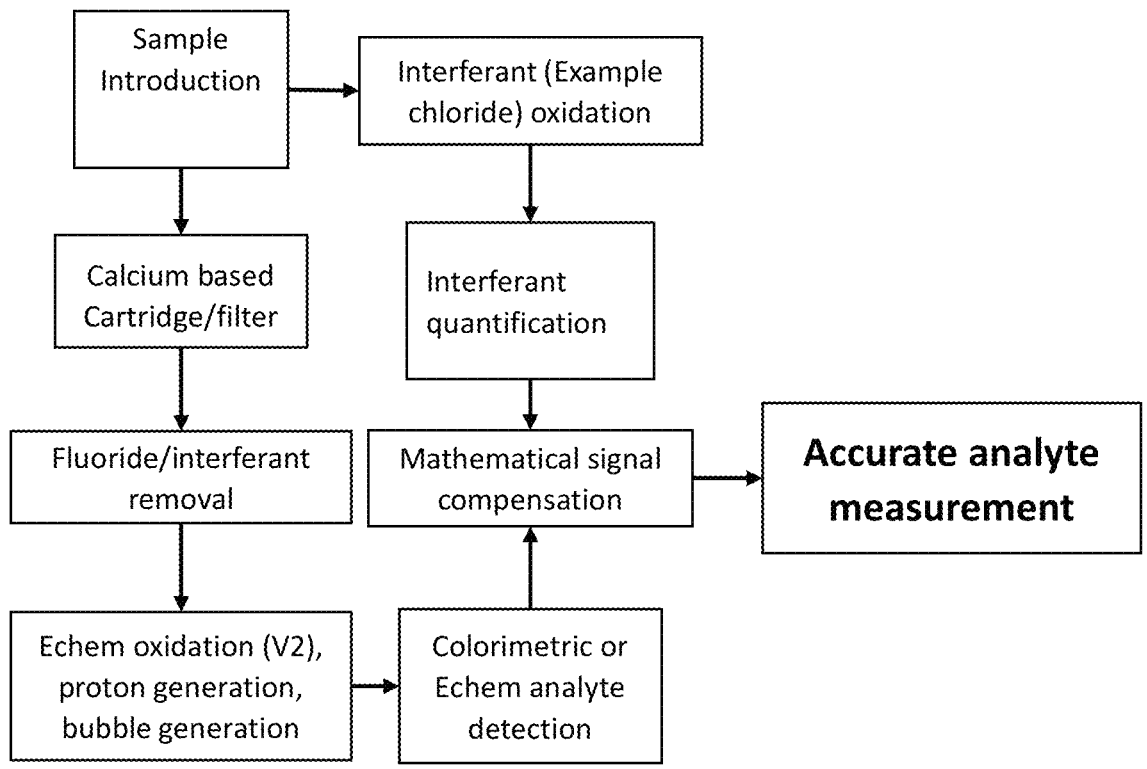
FIG. 4 illustrates an example device for measuring a characteristic of an aqueous sample.

At 104, the system and method may modify the electrical potential based upon the measurement of at least one analyte. In an embodiment, the modifying may be an optimization. A modification or optimization may be an electrical potential or protocol to digest an analyte. Difference electrical potentials may be used for different analytes. In an embodiment, the methods, modification, and optimization described herein may facilitate an accurate analyte measurement. See FIG. 4. The embodiments described regarding optimization may also be used for the initial oxidation and digestions step, but are outlined bellowed for clarity. In other words, the method and system may modify or optimize a digestion at any point in the process. Modification may occur in real time during a digestion. In an embodiment, oxidation, digestion, and electrical potentials may be performed either simultaneously or sequentially for each analyte of interest. Determining the concentration of the higher valent metals not only allows for measurement of materials in the aqueous solution, as described in more detail below, but also allows the power delivered to the system to be modified or optimized. Additionally, the spectroelectrochemical feedback would provide a means to modify or optimize the efficiency of the system and also provide validation of the oxidation capacity of the system. As one example, this feedback would allow optimization of the cell volume. Cell volume may be changed by the movement of the electrodes on the movable blocks. Parameters of the system may be adjusted based upon these findings. For example, the volume of one or more chambers of the system may be changed. A volume may be changed by physically altering the dimension of a chamber. This changing of volume may be accomplished by swapping out a chamber, or by altering the volume of a chamber with a plunger type arrangement. Additionally or alternatively, the volume of aqueous sample may be altered.

As another example, this feedback would allow changes to the distance between electrodes. Referring to FIG. 2 and FIG. 3, a cathode and an anode may be inserted into opposite ends of the lumen of a tube. In an embodiment, a cathode and/or anode may be moved closer together or farther apart. A distance between the electrodes may be changed by successive reactions and preselected for a given reaction measurement. Additionally, or alternatively, a distance between electrodes may be altered in real time. A movement or changing a distance between electrode may also alter a volume of a chamber. In an embodiment, a cathode and an anode may move independently of one another. A movement of the electrode may be automated using a mechanical device such as motors, gears, piston, or the like based on a feedback.

As an additional example, this feedback would allow changes to the concentration of transition metal species. The oxidation of a transition metal may serve to catalyze the oxidation of organics in the aqueous sample. Therefore, altering the concentration of transition metals may alter the kinetics of the system. For example, if an aqueous sample with higher concentration of organics is being measured, a higher concentration of transition metals may be required to provide a proper catalyst component to the system.

In a further example, this feedback would allow modifying the amount of sparging to quantify carbon dioxide from the oxidation of organics in an aqueous sample. Sparging usually involves bubbling a chemically inert gas through a liquid. The sparging technique may be used to remove dissolved gas or gases from a liquid. In an embodiment, the pressure or partial pressure of the system may be altered. Additionally or alternatively, an amount of cavitation due to bubble formation may be altered or perturbed.

As another example, the feedback would allow modification or optimization of the electrical potential applied to the system to optimize the reaction. The electrical potential may be an applied voltage. For example, an aqueous sample to be tested may be introduced to a chamber containing one or more series of electrodes. In an embodiment, the electrical potential applied to the electrodes, and thereby to the aqueous sample, may be a voltage signal. The system may also use a combination of electrical signals, for example, by initially applying a current and then applying a voltage. The system can then measure the electrical response (e.g., current value, voltage value, etc.) that results from the application of the electrical potential to the aqueous solution.

The applied electrical potential may be any electrical potential selected from a waveform group, for example, a pulse, a step, a ramp, a sawtooth, a sine wave, a square, a triangle, a continuous signal, or the like or any combination thereof. Thus, the applied electrical signal may be applied as a constant potential or may be applied as pulses or intermittent electrical potential. In an embodiment, the amplitude may be the same or variable. For example, a first amplitude may be applied and then a second amplitude may be applied. In an embodiment, the period may be the same or variable. The electrical potential may be a preprogrammed waveform, may be altered during a measurement, and/or may be controlled by the system or by a user.

Circuitry may control the electrical signal (e.g., current, voltage, etc.) to one or more series of electrodes such that different electrical signals may be applied to the volume of aqueous sample. In the case that multiple or a series of electrodes are included in the system, each electrode may correspond to a different electrical potential value. For example, a first electrode may correspond to a first electrical signal value, a second electrode may correspond to a second electrical signal value, and the like. Thus, as the system provides electrical signals to each of the electrodes, different components of the aqueous sample may be oxidized. In the case that a single electrode is used, the system may apply different electrical signals to the single electrode, each with an increasing electrical potential value. In either case, after each application of an electrical potential, the system may measure the TOC or COD of the aqueous solution.

At 105, if an analyte of an aqueous sample cannot be measured, the system may introduce an aqueous sample at 101, continue oxidation and digestion at 102, or return to any preceeding step in the method. In other words, oxidation and digestion of an analyte or two or more analytes may be simultaneous or sequential, thus the method may return to a previous step using the same or a different aqueous sample. In an embodiment, the system may apply the same electrical potential as previously applied or may alter the electrical potential to a different amplitude, waveform, or the like.

Additionally, the system may alter parameters as outlined above to modify a digestion of an analyte in the system. The modifications may include changes to an electrical potential, altering a distance between a cathode and an anode, altering the volume of a chamber, altering a volume of the aqueous sample, altering the concentration of the transition metal, or the like.

If, however, at 105, if an analyte of an aqueous sample may be measured, the system may output the characteristic of an aqueous solution at 106. An output may be in the form of a display, storing the data to a memory device, sending the output through a connected or wireless system, printing the output, or the like. The system may be automated. The system may have associated alarms, limits, or predetermined thresholds. For example, if a measured analyte reaches a threshold, the system may trigger an alarm, adjust the characteristic of the aqueous solution, alter the flow of the aqueous solution, or the like. Data may be analyzed in real-time, stored for later use, or any combination thereof. In an embodiment, a measurement of an analyte may be used to modify the method and system at 104. In an embodiment, the method and system may either simultaneously or sequentially oxidize and/or digest an analyte. Therefore, after a measurement of an analyte the system and method may perform one or more further oxidation steps upon the same aqueous sample as described.

Figure 5:
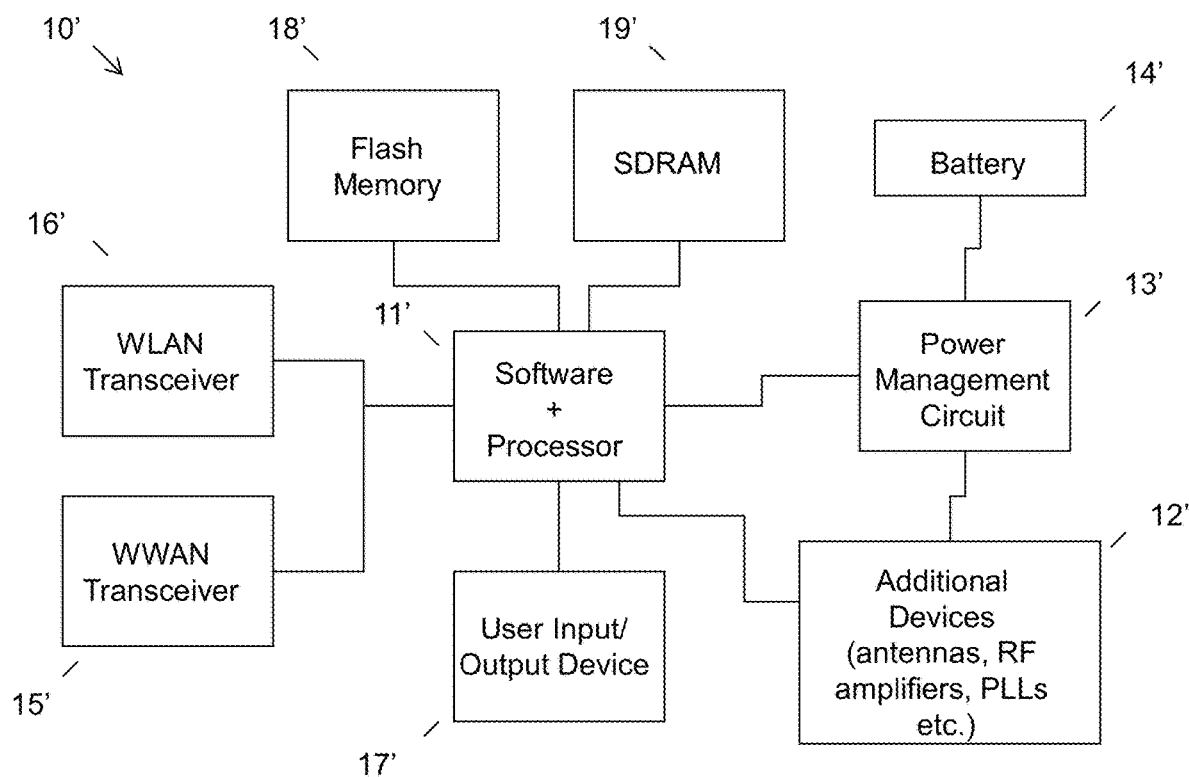
FIG. 5 illustrates another flow diagram of an example measurement of an analyte.

While various other circuits, circuitry or components may be utilized in information handling devices, with regard to an instrument to oxidize or digest an analyte in an aqueous sample according to any one of the various embodiments described herein, an example is illustrated in FIG. 5. Device circuitry 10' may include a measurement system on a chip design found, for example, a particular computing platform (e.g., mobile computing, desktop computing, etc.) Software and processor(s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to oxidize or digest an analyte in an aqueous sample.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device such as illustrated in FIG. 5, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for digesting at least one analyte of an aqueous sample, comprising:
   introducing the aqueous sample comprising the at least one analyte into a digestion device comprising two or more carbon substituted material electrodes, wherein the two or more carbon substituted material electrodes comprise an anode and a cathode, wherein the anode is affixed to an anode block and the cathode is affixed to a cathode block;
   adjusting, using at least one of the anode block and the cathode block, in real time, a distance between the anode block and the cathode block for each of a successive digestion;
   digesting the at least one analyte by applying an electrical potential between the anode and the cathode of the digestion device, wherein the digesting comprises a step-wise disintegration digestion of the at least one analyte prior to a partial digestion of another analyte, wherein the step-wise disintegration digestion adjusts the distance between the anode block and the cathode block preselected for a given reaction measurement, and a volume of the digestion device;
   homogenizing, using a plurality of bubbles, at least one another analyte, wherein the digesting of the at least one analyte generates the plurality of bubbles, wherein the digestion device comprises a gas outlet separate from a digested sample outlet;
   measuring the at least one analyte of the aqueous sample from a digested material, using a measurement device selected from the group consisting of: an electrochemical device and an optical measurement device, wherein the measuring comprises a quantification of an interferant; and
   modifying the electrical potential based upon the measurement of the at least one analyte.

2. The method of claim 1, wherein the digesting electrochemically disintegrates the aqueous sample to a measurable form.

3. The method of claim 1, wherein the interferant is converted by the digesting to a measurable form.

4. The method of claim 3, wherein the interferant comprises chloride, wherein the digesting of the chloride to chlorine that is measurable using a colorimetric method.

5. The method of claim 1, wherein the digesting further comprises production of hydroxyl radicals and oxygen, wherein the oxygen forms bubbles to facilitate homogenization in the aqueous sample.

6. The method of claim 1, wherein the digesting further comprises production of protons which facilitates solubilization of particulates in the aqueous sample.

7. The method of claim 1, wherein the at least one analyte comprises lead, wherein the digesting of the lead generates a plurality of lead species measurable using a colorimetric method, wherein the plurality of lead species is selected from the group consisting of: micro particulate, nano particulate, colloidal, and soluble species.

8. The method of claim 1, wherein the at least one analyte comprises an oligomeric perfluoro compound further comprising at least one of: perfluoro octanoic acid, perfluoro octane sulfonic acid, and perfluoro compounds.

9. The method of claim 8, wherein the digesting of the oligomeric perfluoro compound generates fluoride measurable using a colorimetric method.

10. A measurement device for digesting at least one analyte of an aqueous sample, comprising:
- a digestion device;
- two or more carbon substituted material electrodes, wherein the two or more carbon substituted material electrodes comprise an anode and a cathode, wherein the anode is affixed to an anode block and the cathode is affixed to a cathode block;
- a processor; and
- a memory device that stores instructions executable by the processor to:
- introduce the aqueous sample comprising the at least one analyte into the digestion device comprising the two or more carbon substituted material electrodes;
- adjust, using at least one of the anode block and the cathode block, in real time, a distance between the anode block and the cathode block for each of a successive digestion;
- digest the at least one analyte by applying an electrical potential between the anode and the cathode of the digestion device, wherein the digesting comprises a step-wise disintegration digestion of the at least one analyte prior to a partial digestion of another analyte, wherein the step-wise disintegration digestion adjusts the distance between the anode block and the cathode block preselected for a given reaction measurement, and a volume of the digestion device;
- homogenize, using a plurality of bubbles, at least one another analyte, wherein the digesting of the at least one analyte generates the plurality of bubbles, wherein the digestion device comprises a gas outlet separate from a digested sample outlet;
- measure the at least one analyte of the aqueous sample from a digested material, using a measurement device selected from the group consisting of: an electrochemical device and an optical measurement device, wherein the measuring comprises a quantification of an interferant; and
- modifying the electrical potential based upon the measurement of the at least one analyte.

11. The device of claim 10, wherein the digesting electrochemically disintegrates the aqueous sample to a measurable form.

12. The device of claim 10, wherein the interferant is converted by the digesting to a measurable form.

13. The device of claim 12, wherein the interferant comprises chloride, wherein the digesting of the chloride to chlorine that is measurable using a colorimetric method.

14. The device of claim 10, wherein the digesting further comprises production of hydroxyl radicals and oxygen, wherein the oxygen forms bubbles to facilitate homogenization in the aqueous sample.

15. The device of claim 10, wherein the digesting further comprises production of protons which facilitates solubilization of particulates in the aqueous sample.

16. The device of claim 10, wherein the at least one analyte comprises lead, wherein the digesting of the lead generates a plurality of lead species measurable using a colorimetric method, wherein the plurality of lead species is selected from the group consisting of: micro particulate, nano particulate, colloidal, and soluble species.

17. The device of claim 10, wherein the at least one analyte comprises an oligomeric perfluoro compound further comprising at least one of: perfluoro octanoic acid, perfluoro octane sulfonic acid, and perfluoro compounds.

18. A product for digesting at least one analyte of an aqueous sample, comprising:
- a digestion device;
- two or more carbon substituted material electrodes, wherein the two or more carbon substituted material electrodes comprise an anode and a cathode, wherein the anode is affixed to an anode block and the cathode is affixed to a cathode block; and
- a storage device having code stored therewith, the code being executable by the processor and comprising:
- code that introduces the aqueous sample comprising the at least one analyte into the digestion device comprising the two or more carbon substituted material electrodes;
- code that adjusts, using at least one of the anode block and the cathode block, in real time, a distance between the anode block and the cathode block for each of a successive digestion;
- code that digests the at least one analyte by applying an electrical potential between the anode and the cathode of the digestion device, wherein the digesting comprises a step-wise disintegration digestion of the at least one analyte prior to a partial digestion of another analyte, wherein the step-wise disintegration digestion adjusts the distance between the anode block and the cathode block preselected for a given reaction measurement, and a volume of the digestion device;
- code that homogenizes, using a plurality of bubbles, at least one another analyte, wherein the digesting of the at least one analyte generates the plurality of bubbles, wherein the digestion device comprises a gas outlet separate from a digested sample outlet;
- code that measures the at least one analyte of the aqueous sample from a digested material, using a measurement device selected from the group consisting of: an electrochemical device and an optical measurement device, wherein the measuring comprises a quantification of an interferant; and
- code that modifies the electrical potential based upon the measurement of the at least one analyte.

* * * * *